United States Patent [19]

Arretz et al.

[11] 4,443,310
[45] Apr. 17, 1984

[54] PHOTOINITIATED SYNTHESIS OF MERCAPTANS

[75] Inventors: Emmanuel Arretz; Claude Landoussy, both of Pau; Alfred Mirassou, Poey-de-Lescar; Jean Ollivier, Arudy, all of France

[73] Assignee: Societe Nationale Elf Aquitaine (Production), Courbevoie, France

[21] Appl. No.: 357,068

[22] Filed: Mar. 10, 1982

[30] Foreign Application Priority Data

Mar. 12, 1981 [FR] France ................................ 81 04956
Feb. 22, 1982 [FR] France ................................ 82 02849

[51] Int. Cl.$^3$ .............................................. B01J 19/12
[52] U.S. Cl. ............................ 204/158 R; 204/162 R
[58] Field of Search ............ 204/158 T, 158 R, 162 R

[56] References Cited

U.S. PATENT DOCUMENTS 4,052,283 10/1977 Dannels ........................... 204/158 T
4,233,128 11/1980 Ollivier et al. .................. 204/158 T Primary Examiner—Howard S. Williams
Attorney, Agent, or Firm—Ostrolenk, Faber, Gerb & Soffen

[57] ABSTRACT

Improvement in the photoinitiated synthesis of mercaptans, in which an ethylenic compound is treated with hydrogen sulphide, preferably under pressure, in the presence of ultraviolet radiation and a photoinitiator involves the use of a xanthenic compound, possibly substituted, as the initiator. Preferably, the xanthenic compounds is employed in conjunction with an organic compound of an element of Group V A of the Periodic Classification of the Elements.

19 Claims, No Drawings

PHOTOINITIATED SYNTHESIS OF MERCAPTANS

The present invention relates to an improved process of production of mercaptans starting from olefinic compounds, by reaction of the latter with hydrogen sulphide. It relates more particularly to a new group of initiators allowing this reaction to be carried out under the effect of ultraviolet radiation.

In view of the well-known industrial utility of various mercaptans, methods of preparation of these substances have given rise to numerous studies. One process, which has led to interesting industrial results, consists in direct action of hydrogen sulphide on ethylenic substances, under the effect of ultraviolet radiation. In carrying out this process, it is usual to introduce into the reaction medium promoter agents, particularly organic phosphites, as described for instance in U.S. Pat. No. 3,050,452. The photochemical creation of SH radicals, caused by addition of $H_2S$ to the double bond of the ethylenic compound, implies the utilisation of ultraviolet radiation of short wavelengths, which causes certain disadvantages. In practice, it is necessary to utilise reactants and solvents which are particularly pure and transparent; on the other hand, the optical transmission in the reactor is weak because of the very high coefficient of molecular extinction of hydrogen sulphide; also, the mercaptan synthesised itself absorbs radiation and this causes a considerable slowing of the reactions for slightly elevated degrees of advancement, with formation of sulphur by addition of the mercaptan per se to the double bond of the ethylenic compound. An improvement in this process has been provided by some writers, who have found photoinitiators or photosensitisers capable of being excited in a range of longer wavelengths. Thus, the process described in U.S. Pat. No. 4,052,283 utilises organic photosensitisers containing one or two carbonyl substituents. On the other hand, U.S. Pat. No. 4,140,604 describes activators for the reaction constituted by derivatives of acetophenone.

A much more important advance has been made by the process according to the French patent published under No. 2424907; this process leads to better yields and also permits the use of a wide wavelength band. It consists in adding to the usual reaction medium as a promoter an organic derivative of an element of Group V A of the Periodic Classification of the Elements, at the same time as initiators constituted by benzophenones and/or thiobenzophenones or by one or more derivatives of these aryl ketones. Such ketones, as photochemical promoters employed alone, also can give better results than other known additives. Thus, they allow the advantageous production of mercaptans which it is not possible to obtain with for example trialkyl or triaryl phosphites alone, such as described in U.S. Pat. No. 3,050,452 also, although it is necessary according to this patent to utilise ultraviolet of wavelengths shorter than 300 nm, it is possible to operate above 300 nm in the case of benzo- or thiobenzophenones. The results are remarkably improved when these benzophenones and/or thiobenzophenones are employed in conjunction with phosphites or other organic derivatives of elements of Group V A.

The present invention provides a notable improvement with respect to all these processes of the prior art, in that it allows a substantial increase in the rate of production of the mercaptan starting from an olefinic compound. It has the advantage of being realizable either without a solvent or in a solvent, such as an organic sulphide, a hydrocarbon or an ether. In the case of an organic sulphide, the advantage is all the more marked as the sulphide can be the one obtained as a by-product in the reaction itself.

The new process according to the invention is characterised in that the reaction medium includes a derivative of the xanthene type which acts as an initiator for the formation of the mercaptan starting from an unsaturated compound and $H_2S$, under the effect of ultraviolet radiation.

The initiators according to the invention correspond to the formula:

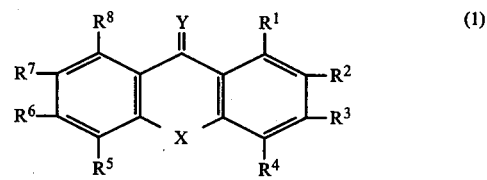

where Y is O or S, while X designates an element O, S or Se, a $-CH_2$, $-CH_2CH_2-$, $SO_2$, CO, CS or NR' group, R' being a hydrocarbon radical or even a tri- or pentavalent phosphorus group, particularly

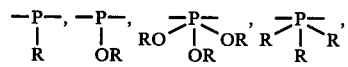

where R designates an alkyl, an aryl, an H or a halogen. The symbols $R^1$ to $R^8$ designate the same or different atoms or groups, such as H, halogen, alkoxy, alkyl and/or aryl.

The preferred range of wavelength is from 300 to 400 nm.

The rate of conversion of the olefinic compound into the mercaptan is even higher, if the xanthene derivative is added in conjunction with an organic compound of an element of group V A of the Periodic Classification, known per se as an initiator for the photochemical reaction in question. Low proportions of initiators suffice, which shows that the xanthane derivative exerts a synergistic action with the organic compound of group V A.

Although organic derivatives of phosphorus, particularly alkyl or aryl phosphites and phosphines, are usually employed at present, due to their commercial availability, the xanthene type additive according to the invention can also be a corresponding organic compound of bismuth, arsenic or antimony; for example, alkyl or aryl arsenites or arsines are suitable as additives.

These derivatives of the xanthene type allow the initiator effect of known agents to be increased, particularly the phosphites mentioned above, and limit the inhibitive action with sulphides, which may be formed by a secondary reaction, may have on the formation of the desired mercaptan. Due to this latter property, the invention makes possible the simultaneous manufacture of mercaptans and sulphides, which can be very useful in certain cases.

The proportions of the xanthane derivative according to the invention to be added to the reaction medium depend upon various factors, particularly the nature of the reactants treated, their concentration in the medium, the presence or absence of a solvent and so on.

Most frequently, these proportions are of the order of 0.0001 to 0.1 mole per liter of reaction medium and in particular 0.0003 to 0.001. The proportion of the compound of the element of Group V A is of the same order.

As regards operative conditions, in particular the temperatures and the $H_2S$/olefin proportions, they are the same as in the corresponding technique already known from prior publications. It is thus not necessary to describe them in detail here; it will merely be noted that the preferred $H_2S$/olefin molar ratios are about 2 to 10, the temperature being maintained between $-10°$ and $+20°$ C., temperatures ranging from $-10°$ to $-5°$ and from $+20°$ to $+35°$ C. nevertheless being utilisable, but less advantageously.

The reaction can be carried out at atmospheric pressure, but it is preferable, to accelerate conversion to the mercaptan, to operate at manometric pressures of 3 to 30 bars.

As regards the nature of the olefins conversion of which into mercaptans can be improved by the process of the invention, reference may be made by way of nonlimitative example to ethylene, propylene, 1-butene, 2-butene, isobutene, 1-pentene, 2-pentene, 1-hexene, 1-heptene, 1-octene, 1-decene, 1-undecene, 1-dodecene, 1-tetradecene, 1-hexadecene, 1-octadecene, 1-eicosene, 1-isopentene, 4-methyl-1-pentene, 3,6-dimethyl-1-heptene, 4-methyl-5-butyl-4-decene, 1,4-diphenyl-2-butene, 3-cyclohexyl-6-eicosene, 4-methyl-2-pentene, 2,4,4-trimethyl-2-pentenecyclopentene, 2,5-diethylcyclopentenecyclohexene, 3-ethyl-cyclohexene, cycloheptene, cyclooctene, 4-vinyl-cyclohexene, alkyl esters of acrylic, methacrylic, crotonic, allylacetic (pentenoic), octylenic, undecylenic, dodecylenic, octadecylenic etc. acids: the esters in question can particularly contain $C_1$ to $C_{30}$ alkyls and more particularly from $C_1$ to $C_8$. The olefinic compounds can include several double bonds, as is the case for example with butadiene or 2,4-hexadiene. The process applies equally to unsaturated compounds carrying substituents, such as halides, hydroxyls, alkoxy groups, carboxyls etc; it can thus be carried out with products such as allyl chloride, allyl alcohol, alkyl or aryl maleates or fumarates and similar compounds.

Unsaturated triple bond compounds are also utilisable in the process of the invention; this is particularly the case with alkynes, such as acetylene which produces vinyl-mercaptan.

Among the compounds according to the invention which are particularly useful, reference can be made for example to the following compounds of formula (1) in which the X and Y positions are the following:

|  | X | Y |
|---|---|---|
| xanthone | O | O |
| xanthione | O | S |
| thioxanthone | S | O |
| anthrone | $CH_2$ | O |
| thioanthrone | $CH_2$ | S |
| dibenzosuberone | $CH_2CH_2$ | O |
| thio-dibenzosuberone | $CH_2CH_2$ | S |
| anthraquinone | CO | O | and their derivatives substituted on the benzene rings, particularly alkyls, alkoxyls or halogens.

As can be seen, the median ring can contain 6 or 7 elements, the latter configuration corresponding to the presence of $-CH_2CH_2-$ at X; if Y is oxygen, the compound, which in this case is dibenzosuberone, forms in the liquid state and is thus easily manipulable and readily accessible industrially. The same applies to thiodibenzosuberone in which Y is a sulphur atom and X is $-CH_2CH_2-$.

A particular advantage of the initiators according to the invention is that if required that can serve under atmospheric pressure; although under these conditions the rate of conversion of the olefin and the hourly production of the mercaptan are less than under a pressure of several bars, they are clearly more effective than the prior initiators, such as organic phosphites alone or acetophenones employed under the same conditions. The absence of secondary products other than the corresponding sulphide allows ready separation of the mercaptan formed and recycling of the olefin and the hydrogen sulphide.

The invention is illustrated by the non-limitative examples which follow.

EXAMPLES 1 TO 5

The reaction is effected in a cylindrical reactor of stainless steel of 245 ml, equipped with a coaxial quartz tube containing UV lamp, the maximum emission of which corresponds to the wavelength of 350 nm. Cooling and agitation of the reaction medium are ensured by an external circuit, constituted by a recirculation pump and an exchanger which allows the temperature of the reaction medium to be maintained at about 10° C. A series of tests are effected, the following parameters of which are kept constant: hydrogen sulphide supply of 250 l/h, 1-dodecene supply of 336 g/h and a pressure of 12 bars. The particular conditions of each test and the results obtained are given in the following table.

TABLE I

| Example No | Initiators and their rates in mole/h | Conversion of Dodecene (%) | Production of Dodecylmercaptan (g/h) |
|---|---|---|---|
| 1 | α-ethoxy-α-phenyl* acetophenone ($2 \cdot 10^{-3}$) | 65 | 222 |
| 2 | α-ethoxy-α-phenyl* acetophenone ($6 \cdot 10^{-3}$) | 74 | 247 |
| 3 | Benzophenone ($5 \cdot 10^{-3}$) + tributylphosphite ($5 \cdot 10^{-3}$) | 77 | 255 |
| 4 | Xanthone ($10^{-4}$) + tributylphosphite ($5 \cdot 10^{-3}$) | 80 | 260 |
| 5 | Thioxanthone ($2 \cdot 10^{-4}$) + tributylphosphite ($5 \cdot 10^{-4}$) | 85 | 270 |

*Initiator according to US-PS 4 140 604.

EXAMPLES 6 AND 7

In the reactor described in Examples 1 to 5, 120 l/h of hydrogen sulphide and 60 l/h of propylene in gaseous form are continuously introduced under a pressure of 8 to 10 bars and, in liquid form, 100 ml of the dimethyl ether of diethylene glycol. The concentration of photo-initiators corresponds to the optimum of the intensity absorbed in the reactor. The temperature of the reaction medium is maintained at about 0° C.

The results of the various tests effected under these conditions are given in the following table.

TABLE II

| Example No | Initiator and its concentration in moles/l | Conversion of Propylene (%) | Production in g/h | |
|---|---|---|---|---|
| | | | n-propyl mercaptan | dipropyl sulphide |
| 6 | Benzophenone 0.03 | 42.2 | 41.1 | 8 |
| 7 | Thioxanthone 0.03 | 63.6 | 58.1 | 19.9 |

EXAMPLES 8 TO 11

Under the same operative conditions as in Examples 6 and 7, benzophenone or thioxanthone are used in association with a phosphite, the rate of which is $19 \times 10^{-4}$, that of the benzophenone being $33 \times 10^{-4}$ and that of the thioxanthone being $1 \times 10^{-4}$ mole per hour.

TABLE III

| Example No | Initiator | Conversion of Propylene (%) | Production in g/h | |
|---|---|---|---|---|
| | | | n-propyl mercaptan | dipropyl sulphide |
| 8 | Benzophenone + tributyl phosphite | 70.9 | 64 | 25 |
| 9 | Thioxanthone Thioxanthone + tributyl phosphite | 81.4 | 72.8 | 34.8 |
| 10 | Thioxanthone + tributyl-phosphine | 95.5 | 85.1 | 51.2 |
| 11 | Thioxanthone + tributyl thiophosphite | 69.9 | 67.1 | 27 |

EXAMPLE 12

The apparatus of the preceding examples is used at a temperature of about $-3°$ C. and a pressure of 9 to 10 bars. 100 ml/h of dipropyl sulphide, $10 \times 10^{-4}$ moles/h of thioxanthone and $1.9 \times 10^{-3}$ mole/h of tributyl phosphite are continuously introduced, as well as, in gaseous form, 120 l/h of $H_2S$ and 60 l/h of propylene. A conversion of 74.8% of the propylene is obtained and a production of 70.3 g/h of n-propylmercaptan. A second test, identical with the first except for the $H_2S$ supply rate which on this occasion is 300 l/h, gives a conversion of 76.9% of the propylene and a production of 93.7 g/h of n-propylmercaptan.

EXAMPLES 13 AND 14

In the reactor of the foregoing examples, two tests are carried out with the following parameters maintained constant: hydrogen sulphide rate of 275 l/h and octene-1 rate of 257 g/h, temperature of $0°$ C. and pressure of 9 bars. The particular conditions of each test and the results obtained are given in the following table:

TABLE IV

| Example No | Initiator and their rates in moles/h | Conversion of Octene (%) | Production of octyl-mercaptan (g/h) |
|---|---|---|---|
| 13 | Benzophenone ($4 \cdot 10^{-3}$) Tributylphosphite ($4 \cdot 10^{-3}$) | 53 | 158 |
| 14 | Thioxanthone ($1.4 \cdot 10^{-4}$) Tributylphosphite ($4 \cdot 10^{-3}$) | 79.6 | 220 |

Results of the same order are obtained with the olefins ethylene, 1-butene, 1-hexene and cyclohexene.

EXAMPLES 15 AND 16

In the reactor of the foregoing examples, 225 cm$^3$ of methylal, 75 cm$^3$ of dibutyl maleate, $6 \times 10^{-3}$ mole of benzophenone and $3.5 \times 10^{-3}$ mole of tributyl phosphine are introduced, as well as 80 liters of hydrogen sulphide. This mixture is irradiated for 4 hours. At the end of this period, the reaction product is analysed. A second test is effected under the same conditions, but with the difference that the benzophenone is replaced by thioxanthone ($2 \times 10^{-4}$ mole). The reaction is carried out in an identical manner.

The following table indicates the rate of conversion of the maleate and the production of dibutyl mercaptosuccinate formed by the reaction concerned:

TABLE V $$BuOOC-CH=CH-COOBu + H_2S \longrightarrow$$

$$BuOOC-\underset{SH}{\underset{|}{CH}}-CH_2-COOBu$$

| Example No | Initiator and their quantities in moles | Conversion of dibutyl maleate (%) | Dibutylmercapto-succinate product (g) |
|---|---|---|---|
| 15 | Benzophenone ($6 \cdot 10^{-3}$) + tributylphosphine ($3.5 \cdot 10^{-3}$) | 90 | 51 |
| 16 | Thioxanthone ($2 \cdot 10^{-4}$) + tributylphosphine ($3.5 \cdot 10^{-3}$) | 98 | 64.5 |

EXAMPLES 17 TO 21

In the apparatus and according to the operative mode of examples 1 to 5, dodecylmercaptan is prepared with, as the initiators, dibenzosuberone (X being $-CH_2CH_2-$ and Y being oxygen) and thiodibenzosuberone (the same X, S atom at Y.)

The following results are obtained.

| Example No | Initiators and their rates in moles/hour | Conversion % of dodecene | Production of dodecyl-mercaptan g/h |
|---|---|---|---|
| 17 | Dibenzosuberone $1.7 \times 10^{-4}$ + tributyl-phosphite $5 \times 10^{-3}$ | 78% | 258 |
| 18 | Dibenzosuberone $1.7 \times 10^{-4}$ + tridecyl-phosphite $6 \times 10^{-3}$ | 79% | 260 |
| 19 | Dibenzosuberone $1.7 \times 10^{-4}$ + tributyl-phosphine $3.5 \times 10^{-3}$ | 88% | 274 |
| 20 | Thiodibenzosuberone $1.7 \times 10^{-4}$ + tributylphosphine $3.5 \times 10^{-3}$ | 87% | 272 |
| 21 | α-ethoxy α-phenyl acetophene $2 \times 10^{-3}$ | 65% | 222 |

(initiators according to US-PS 4 140 604)

It can be seen that the dibenzosuberones, like all the xanthenic derivatives of the foregoing examples, employed in much lower doses than the initiators of the known art, give better results than the latter.

EXAMPLES 22 TO 28

The photochemical "Pyrex" reactor is of the known type with a submerged coaxial lamp; its glass inlet is fritted at the base to ensure good diffusion of the hydrogen sulphide and propylene gases. The irradiated volume is 90 ml. This reactor, thermostated with an external double envelope, operates discontinuously at ambient pressure, the gas inputs being maintained constant throughout the experiment. They are in fact 30 l/h for H₂S and 30 l/h for propylene. The solvent is the diethyl ether of diethylene glycol and the temperature at which it is saturated with hydrogen sulphide and propylene is 10° C.

The photosensitiser concentration corresponds to the optimum of the intensity absorbed in the reactor. The luminous source is a low-pressure mercury lamp of reemission centered at 350 nm. Its power is 8 watts. After 30 minutes, the quantities of mercaptan formed and the percentage of propylene converted are those in the following table.

| Example No | Initiator and its concentration in moles/liter | Production of propylmercaptan g | % of propylene converted |
|---|---|---|---|
| 22 | Dibenzosuberone 0.03 + tributyl-phosphite 0.06 | 4.38 | 20.8% |
| 23 | Dibenzosuberone 0.03 + tridecyl-phosphite 0.06 | 4.35 | 21.1% |
| 24 | Dibenzosuberone 0.03 + tributylphosphine 0.04 | 5.20 | 23% |
| 25 | Thiodibenzosuberone 0.035 + trioctyl-phosphite 0.06 | 4.46 | 21.3% |
| 26 | Thiodibenzosuberone 0.035 + tributylphosphine 0.04 | 5.31 | 22.8% |
| 27 | α-ethoxy α-phenyl acetophenone 0.09 | 3.32 | 19% |
| 28 | Tributylphosphite 0.09 alone | 1.65 | 8.6% |

These results show that the initiators according to the invention have advantages even if the reaction is effected at atmospheric pressure without an excess of H₂S with respect to the olefin.

I claim:

1. In the process of synthesis of mercaptans by the photochemical reaction of an olefinic compound with hydrogen sulphide in the presence of an initiator, the improvement which comprises employing as the initiator an xanthenic type compound of the formula

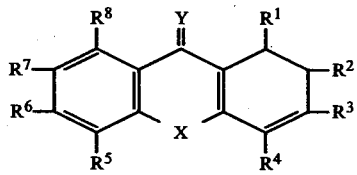

where Y is O or S, X is O, S, Se, —CH₂—, —CH₂CH₂—, SO₂, CO, CS or NR', R' being a hydrocarbon radical,

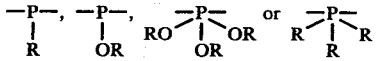

where R designates an alkyl, an aryl, an H or a halogen, the symbols $R^1$ to $R^8$ individually designating H, halogen, alkoxy, alkyl or aryl.

2. Process according to claim 1, characterised in that the light utilized has a wavelength in the range from 300 to 400 nm.

3. Process according to claim 1 or 2, characterised in that an organic compound of an element of Group V A of the Classification of the Elements is employed in conjunction with the initiator of the xanthenic type.

4. Process according to any of claim 3, characterised in that the organic compound of elements of Group V A is an alkyl or aryl phosphite or phosphine.

5. Process according to claim 4 in which the organic compound is a trialkyl phosphate.

6. Process according to claim 5 in which the organic compound is tributyl phosphine.

7. Process according to any of claim 3, characterised in that the element of Group V A is bismuth, arsenic or antimony.

8. Process according to claim 1, characterised in that the reaction medium contains per liter 0.0001 to 0.1 mole of each of the initiators in the reaction medium.

9. Process according to claim 1, characterised in that the olefinic compound treated is halogen, alcohol, carboxyl or alkoxy substituted.

10. Process according to claim 1, characterised in that the olefinic compound treated is an unsaturated acid or ester.

11. Process according to claim 10, characterized in that the unsaturated acid or ester is an alkyl and/or aryl maleate or fumarate.

12. Process according to claim 1, in which the reaction medium contains a solvent, characterised in that this is an organic sulphide.

13. Process according to claim 12, characterised in that the organic sulphide employed as a solvent is the sulphide which is formed as a by-product in the reaction itself.

14. Process according to claim 1, characterized in that the initiator utilized is at least one member selected from the group consisting of xanthone, xanthione, thioxanthone, anthrone, thioanthrone bibenzosuberone and thiodibenzosuberone.

15. Process according to claim 14 in which the reaction temperature is −10° to 35° C., the reaction medium contains per liter 0.001 to 0.1 mol of each of the initiators in the reaction medium and the mercaptan formed is recovered.

16. Process according to claim 15 wherein the amount of initiator is from 0.003 to 0.1 mol per liter of reaction medium, the reaction temperature is between −10° and +20° C., the reaction medium is under a pressure of 3 to 30 bars, and the light utilized has a wavelength in the range from 300 to 400 nm.

17. Process according to claim 1, characterized in that the reaction medium contains per liter 0.001 to 0.1 mole of the initiator.

18. Process according to claim 1 wherein the amount of said xanthenic type initiator is 0.003 to 0.01 mol per liter of reaction medium and the reaction temperature is −10° to +35° C.

19. Process according to claim 18 in which the temperature is between −10° and +20° C. and the reaction medium is under a pressure of 3 to 30 bars.

* * * * *